(12) United States Patent
Chen et al.

(10) Patent No.: US 9,591,990 B2
(45) Date of Patent: Mar. 14, 2017

(54) AUTOMATED CATALOG AND SYSTEM FOR CORRECTION OF INHOMOGENEOUS FIELDS

(75) Inventors: Luke Y. Chen, Roseville, MN (US); Eric S. Olson, Maplewood, MN (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 2649 days.

(21) Appl. No.: 12/047,023

(22) Filed: Mar. 12, 2008

(65) Prior Publication Data
US 2008/0221438 A1   Sep. 11, 2008

Related U.S. Application Data

(63) Continuation-in-part of application No. 11/715,919, filed on Mar. 9, 2007.
(Continued)

(51) Int. Cl.
*A61B 34/20* (2016.01)
*A61B 5/06* (2006.01)
(Continued)

(52) U.S. Cl.
CPC ............... *A61B 5/06* (2013.01); *A61B 34/20* (2016.02); *A61B 90/36* (2016.02); *A61B 5/0422* (2013.01); *A61B 6/503* (2013.01); *A61B 34/10* (2016.02); *A61B 90/90* (2016.02); *A61B 2017/00053* (2013.01); *A61B 2017/00243* (2013.01);
(Continued)

(58) Field of Classification Search
USPC ................. 600/423–427, 431–435, 466–467
See application file for complete search history.

(56) References Cited

U.S. PATENT DOCUMENTS

| 5,297,549 A | 3/1994 | Beatty |
|---|---|---|
| 5,391,199 A | 2/1995 | Ben-Haim |

(Continued)

FOREIGN PATENT DOCUMENTS

| EP | 1743575 | 1/2007 |
|---|---|---|
| EP | 1757227 | 2/2007 |

(Continued)

OTHER PUBLICATIONS

Chui, Haili, "A new algorithm for non-rigid point matching", IEEE Conference on Computer Vision and pattern, vol. 2, pp. 44-51, 2000.
(Continued)

*Primary Examiner* — Joel F Brutus
(74) *Attorney, Agent, or Firm* — Wiley Rein LLP

(57) ABSTRACT

A method for providing a localization system with detailed information regarding a catheter's construction, while at the same time preventing operator input errors, for use in a three-dimensional localization field, including providing a catheter having at least one feature, providing a catheter catalog for use by the localization system, wherein the catheter catalog comprises reference data relating to features of the catheter, placing the catheter into the localization field, creating a map with the localization field, locating the catheter on the map, and correlating features of the catheter within the localization field with measurements made by the localization system when the feature is at various locations.

14 Claims, 12 Drawing Sheets

Related U.S. Application Data

(60) Provisional application No. 60/894,333, filed on Mar. 12, 2007.

(51) Int. Cl.
*A61B 5/042* (2006.01)
*A61B 6/00* (2006.01)
*A61B 17/00* (2006.01)

(52) U.S. Cl.
CPC ............... *A61B 2017/00482* (2013.01); *A61B 2017/00703* (2013.01); *A61B 2017/00725* (2013.01); *A61B 2034/105* (2016.02); *A61B 2034/2051* (2016.02); *A61B 2034/2053* (2016.02); *A61B 2090/364* (2016.02)

(56) References Cited

U.S. PATENT DOCUMENTS

| | | | |
|---|---|---|---|
| 5,480,422 | A | 1/1996 | Ben-Haim |
| 5,546,951 | A | 8/1996 | Ben-Haim |
| 5,568,809 | A | 10/1996 | Ben-Haim |
| 5,662,108 | A | 9/1997 | Budd |
| 5,694,945 | A | 12/1997 | Ben-Haim |
| 5,697,337 | A | 12/1997 | Takahashi et al. |
| 5,697,377 | A | 12/1997 | Wittkampf |
| 5,718,241 | A | 2/1998 | Ben-Haim |
| 5,738,096 | A | 4/1998 | Ben-Haim |
| 5,840,025 | A | 11/1998 | Ben-Haim |
| 5,944,022 | A | 8/1999 | Nardella |
| 5,954,665 | A | 9/1999 | Ben-Haim |
| 5,983,126 | A | 11/1999 | Wittkampf |
| 6,016,439 | A | 1/2000 | Acker |
| 6,066,094 | A | 5/2000 | Ben-Haim |
| 6,104,944 | A * | 8/2000 | Martinelli ............... A61B 5/06 128/899 |
| 6,161,032 | A | 12/2000 | Acker |
| 6,226,542 | B1 | 5/2001 | Reisfeld |
| 6,468,265 | B1 | 10/2002 | Evans et al. |
| 6,640,119 | B1 | 10/2003 | Budd |
| 6,728,562 | B1 | 4/2004 | Budd |
| 6,939,309 | B1 | 9/2005 | Beatty |
| 6,947,785 | B1 | 9/2005 | Beatty |
| 6,978,168 | B2 | 12/2005 | Beatty |
| 6,990,370 | B1 | 1/2006 | Beatty |
| 7,263,397 | B2 | 8/2007 | Hauck |
| 2002/0115941 | A1 * | 8/2002 | Whayne et al. ............... 600/523 |
| 2002/0168618 | A1 * | 11/2002 | Anderson et al. ............ 434/262 |
| 2003/0021381 | A1 | 1/2003 | Koppe |
| 2003/0053697 | A1 * | 3/2003 | Aylward et al. ............... 382/203 |
| 2003/0233037 | A1 * | 12/2003 | Bencini ........................ 600/374 |
| 2004/0097806 | A1 | 5/2004 | Hunter |
| 2004/0138548 | A1 | 7/2004 | Strommer et al. |
| 2004/0254437 | A1 | 12/2004 | Hauck |
| 2004/0258887 | A1 | 12/2004 | Maciag |
| 2005/0080328 | A1 | 4/2005 | Vass et al. |
| 2005/0137478 | A1 | 6/2005 | Younge et al. |
| 2005/0222554 | A1 | 10/2005 | Wallace et al. |
| 2005/0244042 | A1 | 11/2005 | Sirohey |
| 2006/0078195 | A1 | 4/2006 | Vaillant |
| 2006/0079759 | A1 | 4/2006 | Vaillant |
| 2006/0084867 | A1 | 4/2006 | Tremblay |
| 2006/0095022 | A1 | 5/2006 | Moll et al. |
| 2006/0100610 | A1 | 5/2006 | Wallace et al. |
| 2006/0116575 | A1 | 6/2006 | Willis |
| 2006/0210147 | A1 | 9/2006 | Sakaguchi |
| 2006/0253031 | A1 | 11/2006 | Altmann |
| 2007/0003123 | A1 | 1/2007 | Fu |
| 2007/0060833 | A1 | 3/2007 | Hauck |
| 2007/0181139 | A1 | 8/2007 | Hauck |
| 2007/0223794 | A1 | 9/2007 | Preiss et al. |
| 2007/0297657 | A1 | 12/2007 | Mattes et al. |

FOREIGN PATENT DOCUMENTS

| | | |
|---|---|---|
| JP | 03-099630 | 4/1991 |
| JP | 1996-131403 | 5/1996 |
| JP | H08-131403 | 5/1996 |
| JP | 10-149445 | 6/1998 |
| JP | 2002-153443 | 5/2002 |
| JP | 2004-209262 | 7/2004 |
| JP | 2005-078176 | 3/2005 |
| JP | 2005-131367 | 5/2005 |
| WO | 98/19619 | 5/1998 |
| WO | 00/33723 | 6/2000 |
| WO | 02/082375 | 10/2002 |
| WO | 2006/026177 | 3/2006 |
| WO | 2008/112420 | 9/2008 |

OTHER PUBLICATIONS

Ebeling, H., "ASMOOTH: A simple and efficient algorithm for adaptive kernel smoothing of two-dimensional imaging data" Mon. Not. R. Astron. Soc., vol. 368, pp. 65-73, Jan. 2006.

Jain, Ameet Kumar, "FTRAC—A robust fluoroscope tracking fiducial", Medical Physics, vol. 32, No. 10, pp. 3185-3198, Oct. 2005.

Ju, Tao, "Mean Value Coordinates for Closed Triangular Meshes" ACM Transactions on Graphics 24(3), pp. 561-566, Jul. 2005.

Orr, Mark J., "Introduction to radial basis function networks", Centre for Cognitive Science, University of Edinburgh, pp. 1-67, Apr. 1996.

H.J. Johnson et al., "Consistent landmark and intensity-based image registration", IEEE Transactions on Medical Imaging, vol. 21, No. 5, May 2002, pp. 450-461.

John Moody et al.; "Fast Learning in Networks of Locally-Tuned Processing Units"; Neural Computation; vol. 1; No. 2; pp. 281-294; Jun. 1989.

K. Rohr et al.. "Landmark-based elastic registration using approximating thin-plate splines", IEEE Transactions on Medical Imaging, vol. 20, No. 6, Jun. 2001, pp. 526-534.

M.A. Wirth et al., "Point-to-point registration of non-rigid medical images using local elastic transformation methods", Image Processing and its Applications, 1997, Sixth International Conference, vol. 2, Jul. 14, 1997, pp. 780-794.

Martin Auer et al.. "An Automatic Nonrigid Registration for Stained Histological Sections", IEEE Transactions on Image Processing, vol. 14, No. 4, pp. 475-486, Apr. 2005.

Xian-yi cheng et al., "Design and realization of medical image nonrigid matching algorithm", Procedings of the Sixth International Conference on Intelligent Systems Design and Applications (ISDA '06), Oct. 2006.

Bookstein, Fred L., "Principal warps: thin-plate splines and the decomposition of deformations", IEEE transactions on pattern analysis and machine intelligence, vol. 11, No. 6, pp. 507-585. Jun. 1989.

Bookstein, Fred L., abstract for "Thin-plate splines and the atlas problem for biomedical images", Lecture notes in computer science, vol. 511, Jul. 1991.

Bors, Adrian G. et al., "Median radial basis functions neural network", IEEE Transactions on neural networks, vol. 7, Issue 6, Nov. 1996.

Park, J. et al., "Universal approximation using radial-basis-function networks", Neural computation, vol. 3, No. 2, Jun. 1991.

Wiley, David F. et al., "Evolutionary morphing", IEEE Visualization, Oct. 2005.

* cited by examiner

LIST CATHETERS FILTERED BY: — 140

OF ELECTRODES:
ALL
1
2
3
4
5
6
10
20
40
50

OF ELECTRODES — 108

MANUFACTURER:

CATHETER TYPE: [ALL] — 160
BRAND NAME: [ALL] — 170

20 MOST FREQUENTLY USED — 130

| BRAND NAME — 112 | TYPE — 114 | MODEL — 116 | SPACING — 118 | DISTAL LENGTH — 122 |
|---|---|---|---|---|
| THERAPY™ | ABL | 83441 | 2-5-2 | 8 |
| THERAPY™ | ABL | 83441 | 2-5-2 | 8 |
| THERAPY COOL PATH™ | ABL | 83327 | 2-5-2 | 4 |

OF ELECTRODES
4
4
4

FIG.5

LIST CATHETERS FILTERED BY:

OF ELECTRODES: [ALL] — 140, 108
MANUFACTURER: [ALL / SJM / IBI] — 150

CATHETER TYPE: [ALL] — 160
BRAND NAME: [ALL] — 170

130 — 20 MOST FREQUENTLY USED

| BRAND NAME 112 | TYPE 114 | MODEL 116 | SPACING 118 | DISTAL LENGTH 122 | # OF ELECTRODES |
|---|---|---|---|---|---|
| THERAPY™ | ABL | 83441 | 2-5-2 | 8 | 4 |
| THERAPY™ | ABL | 83441 | 2-5-2 | 8 | 4 |
| THERAPY COOL PATH™ | ABL | 83327 | 2-5-2 | 4 | 4 |

FIG.6

LIST CATHETERS FILTERED BY:

OF ELECTRODES: [ALL] — 140

MANUFACTURER: [ALL] — 150

130 — 20 MOST FREQUENTLY USED

CATHETER TYPE:

BRAND NAME:

160 — ALL ABLATION SENSING DIAGNOSTIC REFERENCE LOOP

| # OF ELECTRODES 108 | MANUFACTURER 110 | BRAND NAME 112 | TYPE 114 | SPACING 118 | DISTAL LENGTH 122 |
|---|---|---|---|---|---|
| 4 | IBI/SJM | THERAPY™ | ABL | 2-5-2 | 8 |
| 4 | IBI/SJM | THERAPY™ | ABL | 2-5-2 | 8 |
| 4 | IBI/SJM | THERAPY COOL PATH™ | ABL | 2-5-2 | 4 |

FIG. 7

| | VOLTAGE MEASURED ON X-AXIS | | | | | | | | | |
|---|---|---|---|---|---|---|---|---|---|---|
| | | 0 | 1 | 2 | 3 | 4 | 5 | 6 | 7 | 8 | 9 |
| VOLTAGE MEASURED ON Y-AXIS | 0 | (-3,-5) | (-2,-5) | (-1,-5) | (0,-5) | (1,-5) | (2,-5) | (3,-5) | (4,-5) | (5,-5) | (6,-5) |
| | 1 | (-3,-4) | (-2,-4) | (-1,-4) | (0,-4) | (1,-4) | (2,-4) | (3,-4) | (4,-4) | (5,-4) | (6,-4) |
| | 2 | (-3,-3) | (-2,-3) | (-1,-3) | (0,-3) | (1,-3) | (2,-3) | (3,-3) | (4,-3) | (5,-3) | (6,-3) |
| | 3 | (-3,-2) | (-2,-2) | (-2,-2) | (0,-2) | (1,-2) | (2,-2) | (3,-2) | (4,-2) | (5,-2) | (6,-2) |
| | 4 | (-3,-1) | (-2,-1) | (-1,-1) | (0,-1) | (1,-1) | (2,-1) | (3,-1) | (4,-1) | (5,-1) | (6,-1) |
| | 5 | (-3,0) | (-2,0) | (-1,0) | (0,0) | (1,0) | (2,0) | (3,0) | (4,0) | (5,0) | (6,0) |
| | 6 | (-3,1) | (-2,1) | (-1,1) | (0,1) | (1,1) | (2,1) | (3,1) | (4,1) | (5,1) | (6,1) |
| | 7 | (-3,2) | (-2,2) | (-1,2) | (0,2) | (1,2) | (2,2) | (3,2) | (4,2) | (5,2) | (6,2) |
| | 8 | (-3,3) | (-2,3) | (-1,3) | (0,3) | (1,3) | (2,3) | (3,3) | (4,3) | (5,3) | (6,3) |
| | 9 | (-3,4) | (-2,4) | (-1,4) | (0,4) | (1,4) | (2,4) | (3,4) | (4,4) | (5,4) | (6,4) |

FIG.8

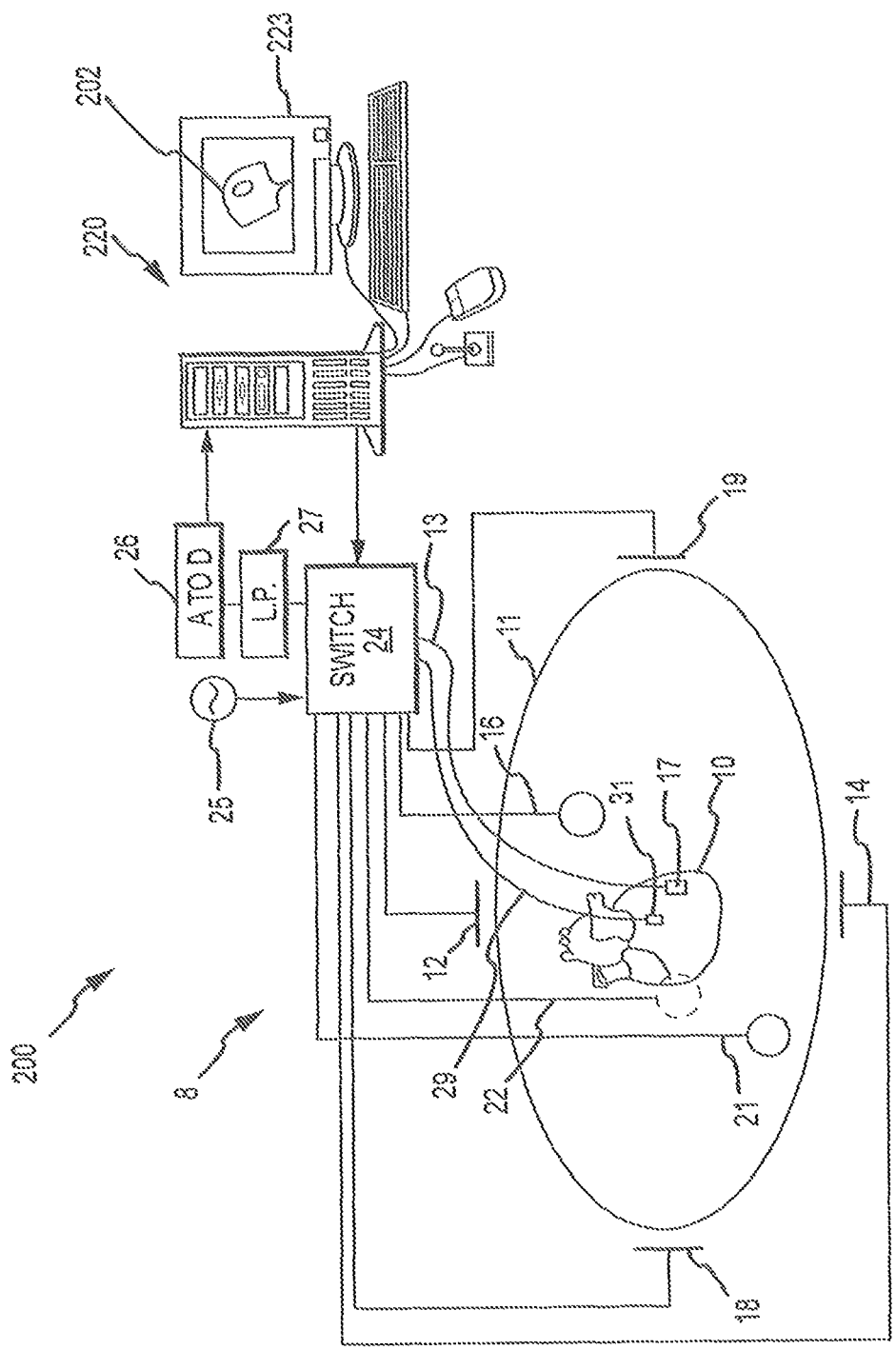

AUTOMATED CATALOG AND SYSTEM FOR CORRECTION OF INHOMOGENEOUS FIELDS

CROSS-REFERENCE TO RELATED APPLICATIONS

This application claims priority to U.S. application No. 60/894,333, filed 12 Mar. 2007, and entitled "Catheter catalog approach for fast catheter settings", which is hereby incorporated by reference as though fully set forth herein. This application is also a continuation-in-part of U.S. application Ser. No. 11/715,919, filed Mar. 9, 2007, and entitled "System and method for correction of inhomogenous fields", which is hereby incorporated by reference as though fully set forth herein. This application is also related to U.S. application Ser. No. 11/715,923, filed Mar. 9, 2007, entitled "System and method for local deformable registration of a catheter navigation system to image data or model", which is hereby incorporated by reference as though fully set forth herein.

BACKGROUND OF THE INVENTION a. Field of the Invention

The instant invention relates to streamlined localization systems that measure position utilizing localization fields with simpler interfaces for the operator. In particular, the instant invention relates to a system and method to allow ready or accurate input of key device characteristics for use in a localization field.

b. Background Art

It is well known to generate heart chamber geometry in preparation for cardiac diagnostic or therapeutic procedures. Often, a mapping catheter is introduced into the heart chamber of interest and moved around within the heart chamber, either randomly, pseudo-randomly, or according to one or more preset patterns. The three-dimensional coordinates are measured using a localization system (sometimes also referred to as a "mapping system," "navigation system," or "positional feedback system"). The localization system measures the coordinates of the mapping catheter within a localization field, typically by relating a characteristic of the localization field, such as a voltage, experienced by the mapping catheter to a location of the catheter within the field. A similar process may be used to measure the position of any object, such as an ablation catheter or other medical device, within the localization field.

After mapping is substantially complete a map may be generated for use in subsequent procedures. Both during the mapping process, and after mapping, the operator may wish to be able to visualize the location of a catheter on the map. Accordingly, a localization system may provide a visual representation of the current position for catheter or other medical device. This visual representation may take many forms, including an computer generated image of the actual catheter, an arrow representing the catheter, and other forms known in the art. The visual representation may seek to provide information to the operator, including where electrodes or other portions of the catheter are located, which direction the catheter is moving, and the relative size of the catheter in relation to the heart chamber. In addition, data about the catheter construction may help inform the accuracy of the image. However, accurately providing certain information requires detailed information on the catheter's construction.

BRIEF SUMMARY OF THE INVENTION

It is therefore desirable to be able to provide a localization system with detailed information regarding a catheter's construction, while at the same time preventing operator input errors.

A method for providing a localization system with detailed information regarding a catheter's construction, while at the same time preventing operator input errors, for use in a three-dimensional localization field, including providing a catheter having at least one feature, providing a catheter catalog for use by the localization system, wherein the catheter catalog comprises reference data relating to features of the catheter, placing the catheter into the localization field, creating a map with the localization field, locating the catheter on the map, and correlating features of the catheter within the localization field with measurements made by the localization system when the feature is at various locations.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 5 depicts a drop down menu for the catheter catalog of FIG. 3.

FIG. 6 depicts a drop down menu for the catheter catalog of FIG. 3.

FIG. 7 depicts a menu for the catheter catalog of FIG. 3.

FIG. 8 illustrates a representative lookup table in two dimensions.

FIG. 11 schematically illustrates a system for registering a catheter navigation system to a three-dimensional image.

DETAILED DESCRIPTION OF THE INVENTION

The present invention provides a method and system for providing a localization system with detailed information regarding a catheter's construction, while at the same time preventing operator input errors.

Localization fields are often employed in procedures carried out within a human body, and in particular in cardiac diagnostic and therapeutic procedures. Therefore, for purposes of illustration, the invention will be described in detail in the context of a localization system utilized in a cardiac electrophysiology procedure. It is contemplated, however, that the present invention may be practiced to good advantage in other contexts, including, for example, to measure internal distortions in a manufacturing environment. Further, though the invention will generally be illustrated in two-dimensions, one of ordinary skill in the art will appreciate how to apply the principles described herein in any number of dimensions. For example, the present invention may be practiced in the time domain in order to compensate for changes in localization fields that occur with respiration and cardiac motion.

Figure 1:
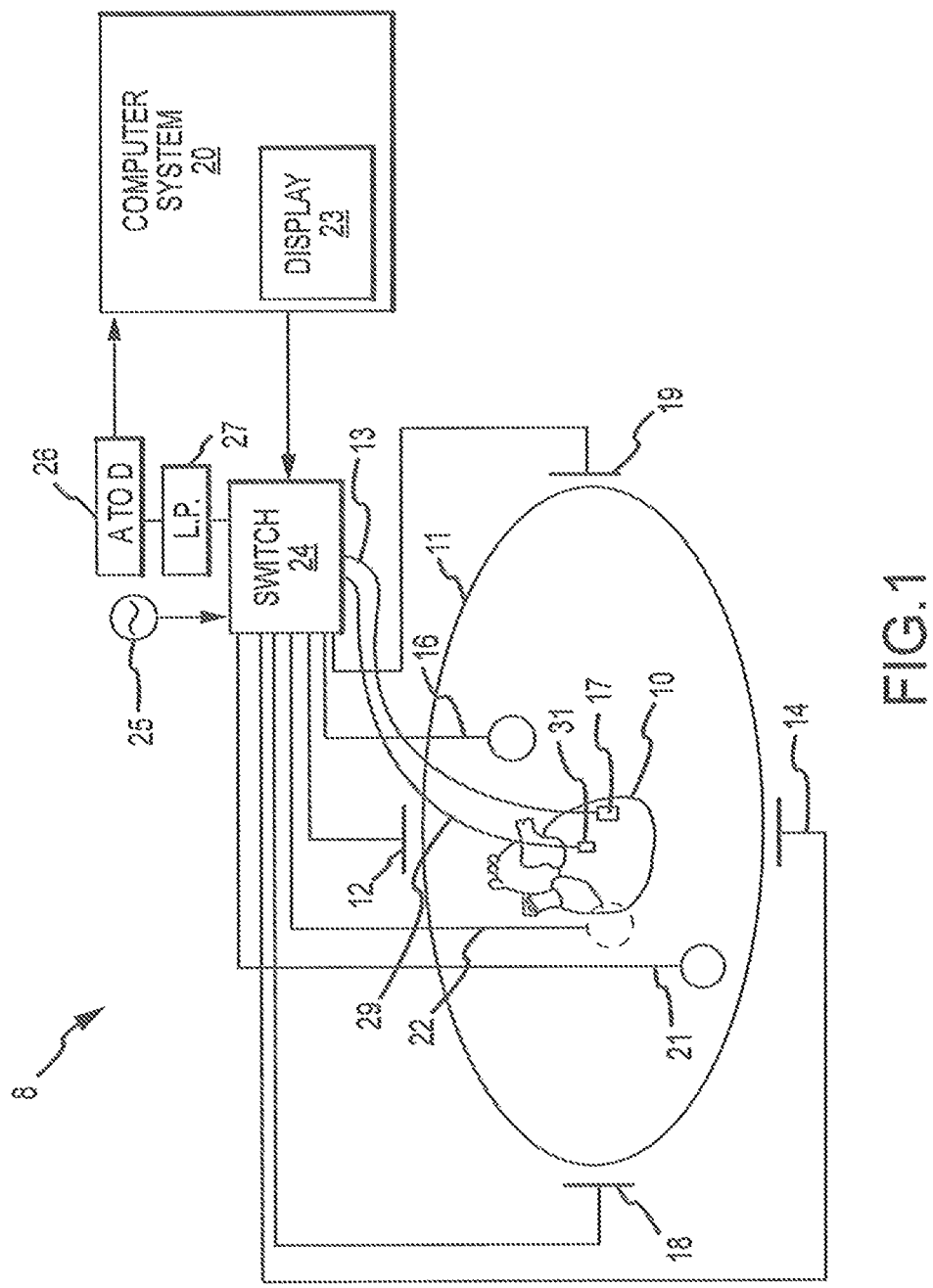
FIG. 1 is a schematic diagram of a localization system utilized in an electrophysiology study.

FIG. 1 shows a schematic diagram of a localization system 8 for conducting cardiac electrophysiology studies by navigating a cardiac catheter and measuring electrical activity occurring in a heart 10 of a patient 11 (depicted schematically as an oval for simplicity) and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface, and store the measured data in association with location information for each measurement point at which the electrophysiology data was measured, for example to create a diagnostic data map of the patient's heart 10. As one of ordinary skill in the art will recognize, and as will be further described below, localization system 8 determines the location of objects, typically within a three-dimensional space, and expresses those locations as position information determined relative to at least one reference.

For simplicity of illustration, the patient 11 is depicted schematically as an oval. Three sets of surface electrodes (e.g., patch electrodes) are shown applied to a surface of the patient 11, defining three generally orthogonal axes, referred to herein as an x-axis, a y-axis, and a z-axis. The x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram (ECG) system leads in place. This ECG information is available to the system 8, although not illustrated in FIG. 1.

A representative catheter 13 having at least one electrode 17 (e.g., a distal electrode) is also shown. This representative catheter electrode 17 is referred to as the "roving electrode," "moving electrode," or "measurement electrode" throughout the specification. Typically, multiple electrodes on catheter 13, or on multiple such catheters, will be used. In one embodiment, for example, localization system 8 may comprise up to sixty-four electrodes on up to twelve catheters disposed within the heart and/or vasculature of the patient. Of course, this embodiment is merely exemplary, and any number of electrodes and catheters may be used within the scope of the present invention.

Figure 2:
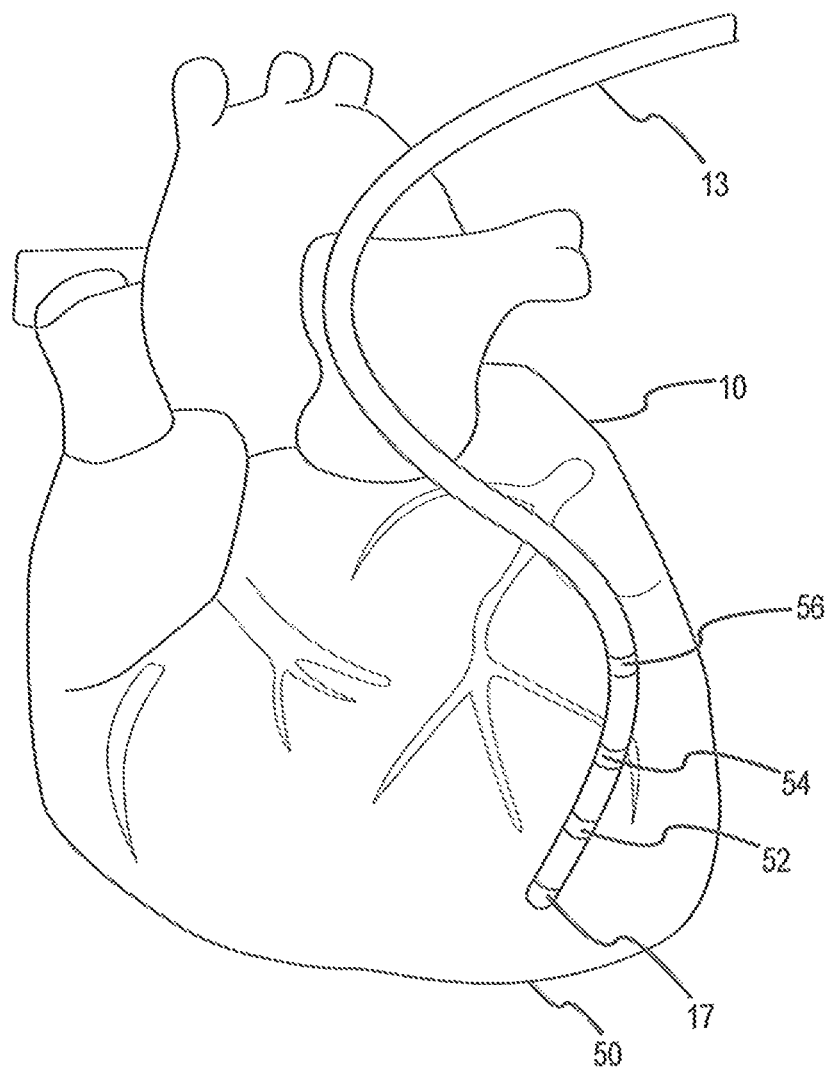
FIG. 2 depicts an exemplary catheter used in an electrophysiology study.

For purposes of this disclosure, an exemplary catheter 13 is shown in FIG. 2. In FIG. 2, catheter 13 extends into the left ventricle 50 of the patient's heart 10. Catheter 13 includes electrode 17 on its distal tip, as well as a plurality of additional measurement electrodes 52, 54, 56 spaced along its length. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by localization system 8.

Returning now to FIG. 1, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to the multiplex switch 24, and the pairs of surface electrodes are selected by software running on a computer 20, which couples the surface electrodes to a signal generator 25. The computer 20, for example, may comprise a conventional general-purpose computer, a special-purpose computer, a distributed computer, or any other type of computer. The computer 20 may comprise one or more processors, such as a single central processing unit (CPU), or a plurality of processing units, commonly referred to as a parallel processing environment, which may execute instructions to practice the various aspects of the present invention described herein. A pair of electrodes, for example electrodes 18 and 19, may be excited by the signal generator 25 and they generate a field in the body of the patient 11 and in the heart 10. During the delivery of the current pulse, the remaining patch electrodes 12, 14, 19, 22 are referenced to the belly patch electrode 21, and the voltages impressed on these remaining electrodes 12, 14, 19, 22 are measured by the analog-to-digital or A-to-D converter 26. Suitable lowpass filtering of the digital data may be subsequently performed in software to remove electronic noise and cardiac motion artifact after suitable low pass filtering in filter 27. In this fashion, the various patch electrodes 18, 19, 12, 14, 19, 22 are divided into driven and non-driven electrode sets. While a pair of electrodes is driven by the signal generator 25, the remaining non-driven electrodes are used as references to synthesize the orthogonal drive axes.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. Preferably, the coordinate system is a three-dimensional (x,y,z) Cartesian coordinate system, though the use of other coordinate systems, such as polar, spherical, and cylindrical coordinate systems, is within the scope of the invention.

If a roving electrode, e.g., 17 is swept around in the heart chamber while the heart 10 is beating, a large number of electrode locations are collected. These data points are taken at all stages of the heartbeat and without regard to the cardiac phase. Since the heart 10 changes shape during contraction, only a small number of the points represent the maximum heart volume. By selecting the most exterior points, it is possible to create a "shell" representing the shape of the heart 10, e.g., at its maximum heart volume. The shell may be created by computer system 20. The location attribute of the electrodes within the heart 10 are measured while the electric field is impressed on the heart 10 by the surface patch electrodes 18, 19, 12, 14, 19, 22. This shell is then provided to display 23 to provide an image of the heart 10.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described in co-pending U.S. patent application Ser. No. 11/227,580, filed on 15 Sep. 2005, which is also incorporated herein by reference in its entirety.

In summary, the system 8 first selects a set of surface electrodes and then drives them with current pulses. While the current pulses are being delivered, electrical activity, such as the voltages measured at least one of the remaining surface electrodes and in vivo electrodes, is measured and stored. Compensation for artifacts, such as respiration and/or impedance shifting, may be performed as indicated above.

In a preferred embodiment, the localization/mapping system is the EnSite NavX™ navigation and visualization system of St. Jude Medical, Atrial Fibrillation Division, Inc., which generates the electrical fields described above. Other localization systems, however, may be used in connection with the present invention, including for example, the CARTO navigation and location system of Biosense Webster, Inc., or the AURORA® system of Northern Digital Inc., both of which utilize magnetic fields rather or in addition to electrical fields. The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

The fields generated by localization system 8, whether an electrical field (e.g., EnSite NavX™), a magnetic field (e.g., CARTO, AURORA®), or another suitable field, may be referred to generically as "localization fields," while the elements generating the fields, such as surface electrodes 12, 14, 16, 18, 19, and 22 may be generically referred to as "localization field generators." As described above, surface electrodes 12, 14, 16, 18, 19, and 22 may also function as detectors to measure the characteristics of the localization field (e.g., the voltages measured at roving electrodes 17, 52, 54, 56). Though the present invention will be described primarily in the context of a localization system that generates an electrical field, one of ordinary skill in the art will understand how to apply the principles disclosed herein in other types of localization fields (e.g., by replacing electrodes 17, 52, 54, 56 with coils to detect different components of a magnetic field).

It is desirable to provide the operator with an image of both the heart 10 and of any medical instruments on display 23. In particular, it is desirable to provide an image that shows the operator where the medical instrument is in relation to heart 10. E.g., the operator may wish to navigate catheter 13 within a particular chamber of heart 10, and to a specific location within heart 10. the operator may wish to move an electrode 17, e.g., an ablation electrode, to a location for the purposes of a medical procedure, e.g., ablation, at a particular location in the heart.

Accordingly, localization systems will determine the location of the catheter in the heart. As discussed above, in one method the measured voltages may be used to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. Preferably, the coordinate system is a three-dimensional (x,y,z) Cartesian coordinate system, though the use of other coordinate systems, such as polar, spherical, and cylindrical coordinate systems, is within the scope of the invention.

Using the data from the measured voltages, computer 20 can provide display 23 with a graphical representation of catheter location. However, using the voltages alone may result in an inhomogenous localization field, and accordingly both the location of the catheter and the representation of the catheter cat be distorted. For example, catheter 13 may have four electrodes, 17, 52, 54, and 56, with uniform 2 mm spacing between adjacent electrodes. However, a distorted localization field may represent electrode 17 as being 2.2 mm from electrode 52, and represent electrode 52 as 1.8 mm from electrode 54.

Figure 3:
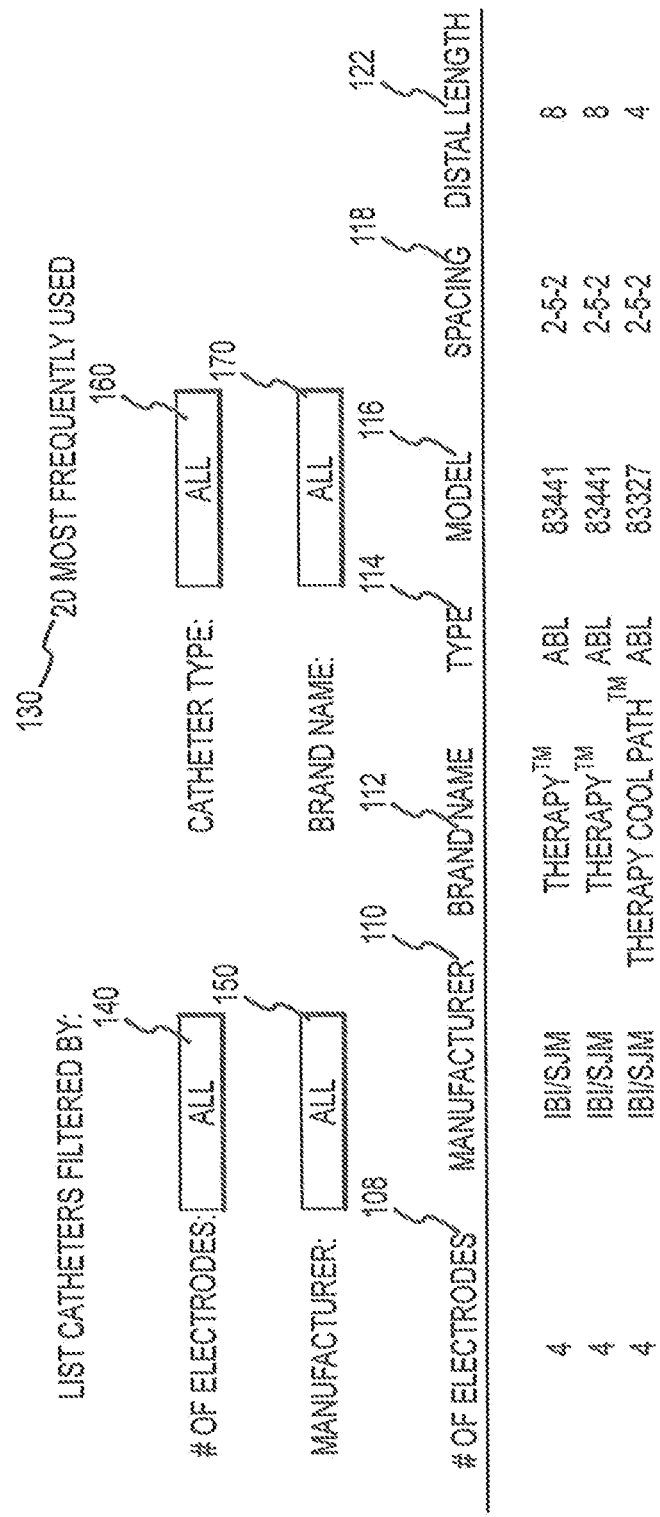
FIG. 3 depicts a representative interface for a catheter catalog
Figure 4:
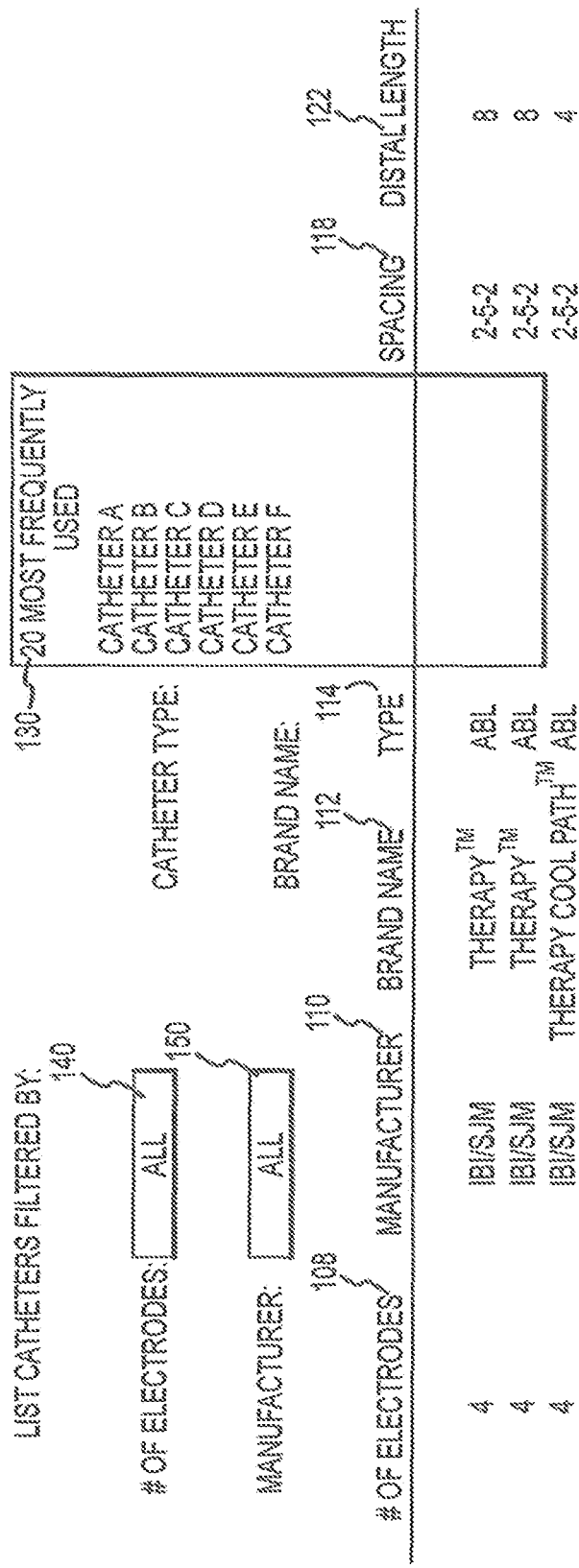
FIG. 4 depicts a drop down menu for the catheter catalog of FIG. 3.

In order to correct for potential distortions, localization system 8 may provide a catheter catalog 100, illustrated in FIG. 3. Catheter catalog 100 provides the operator with a list of known catheters and their characteristics. The information held in catheter catalog 100 can include the number of electrodes 108, the catheter manufacturer 110, the catheter brand name 112, the catheter type 114, the catheter model number, 116, the electrode spacing 118, or the distal end length, 122, It can also include other information, such as the catheter length, the catheter diameter, e.g., French size, how often the catheter has been used with the localization system, catheter inventory, etc. The catheter catalog 100 can be updated remotely, and it can be updated locally, e.g., by the operator. It can also learn the most frequently used catheters 130, and be set to display these catheters first for ease of use. In a preferred embodiment, the catheter catalog is a database file, e.g., an SQL file, stored on computer system 20.

With reference to FIGS. 3-7, to select a catheter, the operator may utilize drop down menus for the most frequently used catheters 130 (FIG. 4), the number of electrodes 140 (FIG. 5), the manufacturer 150 (FIG. 6), the catheter type 160 (FIG. 7), the brand name 170, or any other characteristic. In addition, the catheter characteristics may be modified for any catheter. However, having values preset for each catheter reduces or eliminates operator error, and reduces operator input and setup time. In addition, accurate information regarding electrode spacing allows for improved mapping and improved procedures.

The catheter catalog can contain information relating to any catheter feature, including electrodes, thermisters or thermocouples, arrays, irrigation ports, balloons, guide wires, needles, lumens, shape memory wires, catheter walls, catheter shape, catheter construction, and the like. Accordingly, the catheter catalog may be referenced to provide a location for any of these features. Once the catheter is located on the map created by the localization system, e.g., by an electrical field, a magnetic field, or another suitable field, not only can the element so located be mapped, but any other element provided for in the catheter catalog may be so mapped. By provided the relevant catheter characteristics automatically, operator error is eliminated, and the operator setup time is greatly reduced.

For example, while a thermistor may not show up in a magnetic field generated map generated in the CARTO® system, once the catheter location is established in that system, a thermistor in the catheter may be located through reference to the catheter catalog and its spatial relationship the element that is located in the magnetic field. This will allow the operator to know precisely what portion of the heart the thermistor is closest too, and accordingly better gauge the import of the temperature readings. Likewise, knowing—and visualizing on display 23—the precise location of other catheter features may allow for numerous procedural benefits that are not detailed here. By provided the relevant catheter characteristics automatically, operator error is eliminated, and the operator setup time is greatly reduced.

In addition to allowing for precise location of catheter features, the catheter catalog allows for more precise mapping.

For example, the data from catheter catalog 100 may be used to correct for inhomogeneous field issues. Localization system 8 may be provided with a three-dimensional lookup table that includes reference data correlating locations of an object within the localization field with measurements made by the localization system when the object is at various locations within the localization field. For example, as described above, the voltages measured at roving electrodes 17, 52, 54, 56 within the electrical field generated by surface electrode pairs 12/14, 18/19, and 16/22 may be utilized to determine the location of electrodes 17, 52, 54, 56 within the localization field, such that the reference data in the lookup table may include information relating voltage readings to physical location within the localization field. In effect, the lookup table defines a three-dimensional coordinate system for the localization field, including a plurality of reference points (e.g., the cells or nodes of the lookup table) that serve as references for defining or identifying the observed location of an object located within the localization field. In some embodiments of the invention, the three-dimensional lookup table, and therefore the three-dimensional coordinate system, is created by a modeling processor, which may be incorporated within computer 20, and utilizes data from the catheter catalog.

In the initial stages of a procedure, the lookup table may include predicted reference data for a completely homogenous localization field. Such a lookup table is illustrated (in two dimensions) in FIG. 8. For purposes of illustration only, the lookup table assumes that 9 volts are applied across the surface electrodes of the x-axis (patch electrodes 12, 14) and the y-axis (patch electrodes 18, 19), and that the surface electrodes are each separated by a distance of 9 units, such that a change of 1 volt is equivalent to a movement of 1 unit. Further, the lookup table assumes that the origin (0,0), defined, for example, by reference electrode 31, experiences a voltage of 3 volts on the x-axis and 5 volts on the y-axis. Voltages greater than the voltage measured at reference electrode 31 are defined as positive, while voltages less than the voltage measured at reference electrode 31 are defined as negative. Each entry within the lookup table (e.g., each cell or node of the lookup table) defines a reference point for the coordinate system relative to which localization system 8 measures positions of objects within the localization field. Though only integer values are depicted in the lookup table of FIG. 8, it is contemplated that the lookup table utilized in practicing the invention may have additional detail (that is, the axes of the lookup table may be graduated in any interval). Of course, it is also contemplated that intermediate values (that is, values not corresponding exactly to a cell within the lookup table) may be determined through interpolation, preferably utilizing an interpolation function that is continuous between nodes of the lookup table.

As one of ordinary skill in the art should recognize, contrary to the assumption utilized to originally populate the nodes of the three-dimensional lookup table, the localization field generated by localization system 8 may not be perfectly homogeneous. The predicted reference data used to initially populate the lookup table may therefore be imprecise, and may introduce error into the measured positions of roving electrodes 17, 52, 54, 56 or another object within the localization field. It is desirable to correct for these inhomogeneities so as to minimize measurement error, thereby improving the accuracy and precision of localization system 8.

After placing the catheter into the localization field, localization system 8 may be utilized to determine the location of each of the plurality of electrodes 17, 52, 54, 56 based on the data in the lookup table. The locations of electrodes 17, 52, 54, 56, as determined by the reference data in the lookup table, may then be used to calculate an observed distance between pairs of electrodes, and preferably between pairs of adjacent electrodes such as electrodes 17 and 52.

For example, suppose localization system 8 measures a voltage of 7 volts on the x-axis and 6 volts on the y-axis at electrode 17, and a voltage of 7 volts on the x-axis and 8 volts on the y-axis at electrode 52. The lookup table, as originally populated for a homogenous localization field, indicates that electrode 17 is located at coordinates (4,1), while electrode 52 is located at coordinates (4,3). The observed distance between electrodes 17 and 52 is therefore 2 units, as given by the equation $d=\sqrt{(x_1-x_2)^2+(y_1-y_2)^2}$, where d is the distance between two coordinate points $(x_1, y_1)$ and $(x_2, y_2)$.

As described above, the actual distance between electrodes 17 and 52 is known based on values from the catheter catalog. The observed distance between electrodes 17 and 52 may differ from the actual distance due to inhomogeneities in the localization field. Accordingly, an error processor, which may be part of computer 20, preferably compares the observed distance to the actual distance in order to determine and output an error signal. The error signal, in turn, may be used to adjust the reference data in the three-dimensional lookup table in order to more accurately measure the spacing of electrodes 17, 52, 54, 56. A correction processor, which may be incorporated in computer 20, and which is preferably coupled to the modeling processor and the error processor, may adjust the reference data to reduce the error signal (that is, to reduce the difference between the observed distance and the actual distance).

It should be understood that, though electrodes 17 and 52 are used herein as an example, the error signal preferably incorporates information from all electrodes 17, 52, 54, 56 as catheter 13 moves through the localization field over time, thereby providing a plurality of observed distances between pairs of electrodes that may be compared to the actual distances between those electrodes. This may be done in real-time or on pre-recorded data.

In some embodiments of the invention, a Kernel function is used to adaptively update the reference data in the three-dimensional lookup table. Preferably, the Kernel function is a decay function, in that updates to the reference data diminish in magnitude as the adjustment point increases in distance from the locations of the plurality of electrodes. That is, the reference point or node in the lookup table closest to the observed coordinate will be updated the most, those reference points or nodes in the lookup table directly adjacent to the observed coordinate will be updated next-most, and so on; those reference points or nodes in the lookup table furthest from the observed coordinate will be updated the least, or potentially not at all.

One suitable Kernel function is a derivative of a Gaussian curve, and may be given by the general formula $$K(x) = axe^{-\frac{x^2}{2\sigma^2}}.$$

Figure 9:
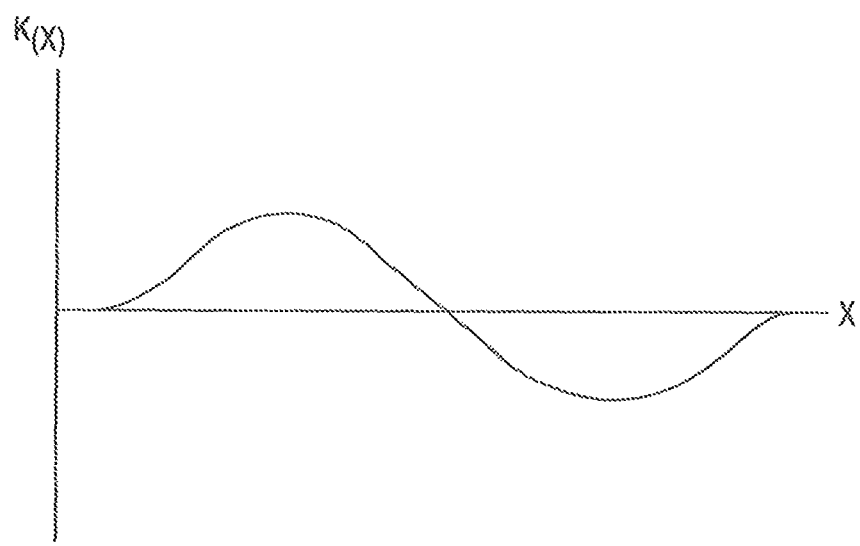
FIG. 9 illustrates a Kernel function.

This Kernel function is illustrated in FIG. 9, and has both positive and negative lobes that decay smoothly to zero as distance from the center of the lobe increases. It is contemplated, however, that any Kernel function having both a positive lobe and a negative lobe, each of which decays smoothly to zero as distance from the center of the lobe increases, may be utilized to practice the present invention.

Thus, for example, if the observed distance between electrodes is less than the known distance between electrodes, the error signal is negative, and the distance separating reference points within the coordinate system may be increased (e.g., the localization field may be stretched). Similarly, if the observed distance between electrodes is greater than the known distance between electrodes, the error signal is positive, and the distance separating reference points within the coordinate system may be reduced (e.g., the localization field may be contracted).

Figure 10A:
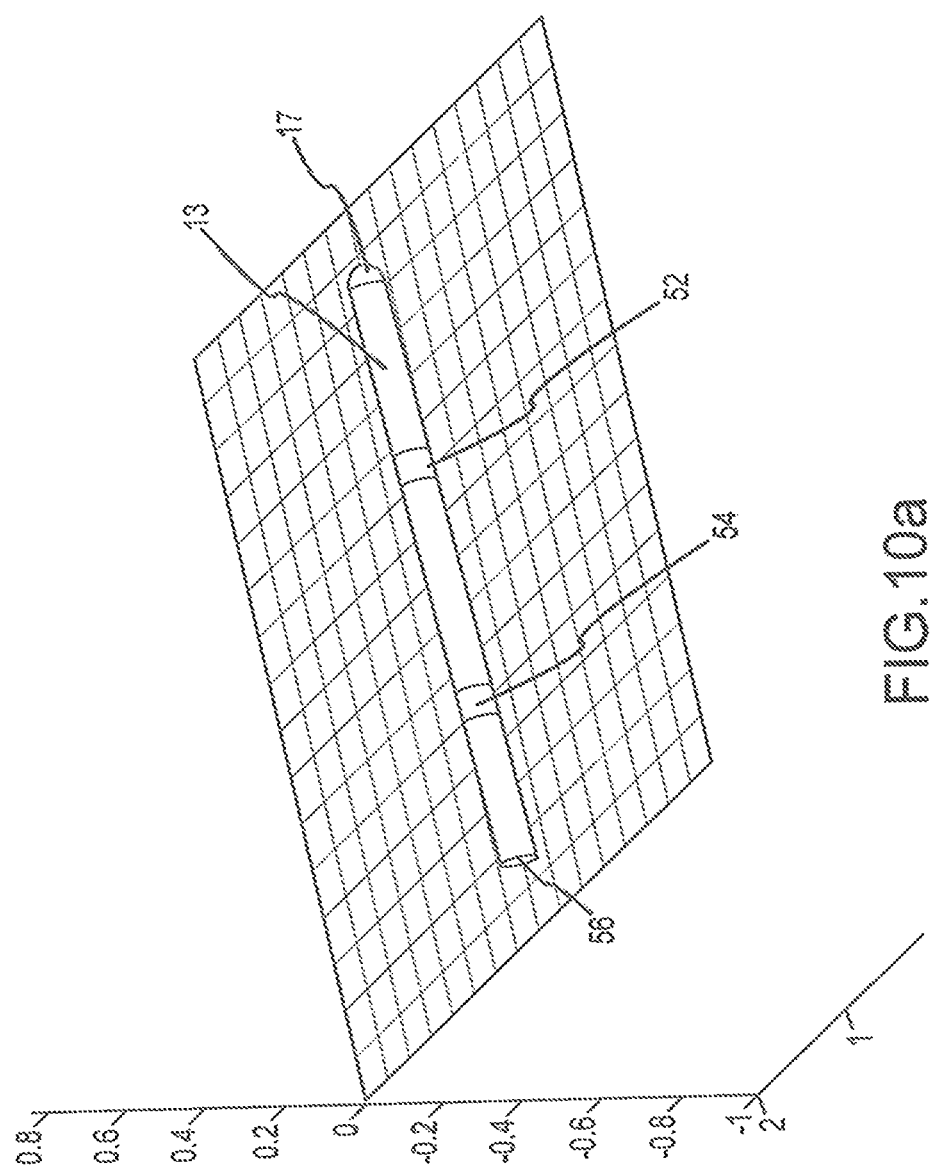
FIG. 10a illustrates a catheter as observed by a localization system assumed to be homogeneous.
Figure 10B:
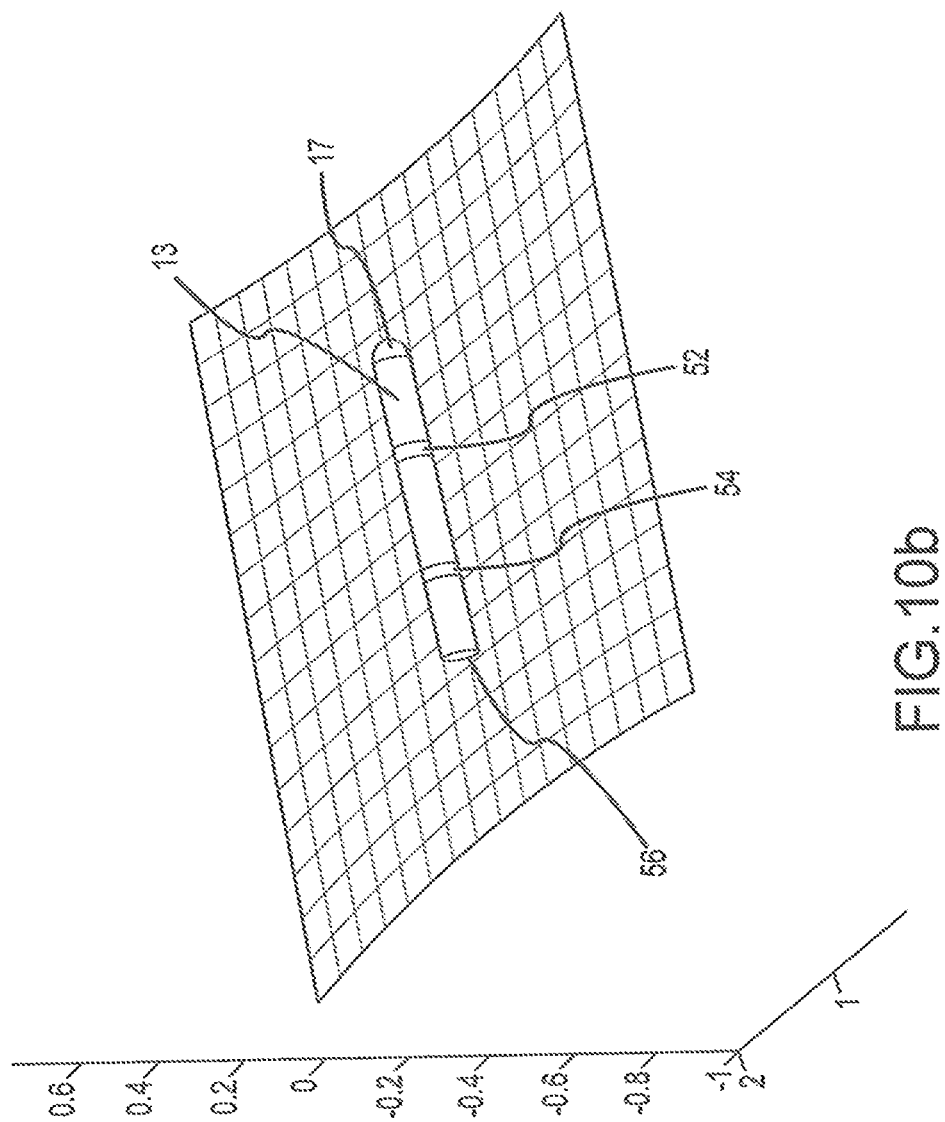
FIG. 10b illustrates the catheter of FIG. 10a as observed after an iteration of updates has been performed on the reference points for the localization system.

The latter case is illustrated in FIGS. 10*a* and 10*b*. FIG. 10*a* illustrates catheter 13 and electrodes 17, 52, 54, 56 as measured within the localization field created by localization system 8. The localization field is illustrated as a grid. The observed distance between electrodes 17 and 52 is about 4 units, the observed distance between electrodes 52 and 54 is about 5 units, and the observed distance between electrodes 54 and 56 is about 3.5 units. Assume, however, that the known distance between electrodes is only 1 unit, such that the observed values are too large (e.g., catheter 13 appears to have stretched beyond its known dimensions). The Kernel function will accordingly update the reference data within the three-dimensional lookup table to effectively contract the localization field. As shown in FIG. 10*b*, which represents the localization field of FIG. 10*a* after a single iteration of the Kernel function, the reference points (e.g., the grid) have been contracted, and the entries within the lookup table have been updated, such that the observed distance between electrodes 17 and 52 is about 2.5 units, the observed distance between electrodes 52 and 54 is about 3 units, and the observed distance between electrodes 54 and 56 is about 2 units.

As should be clear from the foregoing discussion, a single iteration of the Kernel function may not account for all inhomogeneities in the localization field. Preferably, comparatively small adjustments to the reference data are made during each iteration of the Kernel function to approach an optimal solution with a diminishingly small error signal. It is also contemplated that these iterations may be performed in real-time while catheter 13 is moved within the patient's heart 10, for example while collecting a plurality of geometry points from which a cardiac surface model will be generated, and the geometry points so collected may also be updated along with the reference data in the three-dimensional lookup table.

After a sufficient number of iterations of the Kernel function have been performed, the three-dimensional lookup table will have been updated to approach an optimal solution with a diminishingly small error signal. An object may then be placed in the localization field, and the location of the object may be accurately and precisely determined using the adjusted data in the three-dimensional lookup table.

More generally, the present invention may be utilized to locate an object in a defined space, even if that object lacks elements having a known spacing as would typically be the case for electrodes 17, 52, 54, 56. As described above, the localization field may have a defined three-dimensional coordinate system including a plurality of reference points that serve as references for defining an observed location of an object within the localization field. A calibration tool or object (for example, catheter 13) having a plurality of calibration elements (for example, electrodes 17, 52, 54, 56) spaced at known distances may be placed into the localization field. Reference information, such as position information for each of the calibration elements, may then be received relative to the three-dimensional coordinate system, and an observed spacing distance may be calculated for at least two of the calibration elements. A calibration signal may then be generated based on a comparison of the observed spacing distance and the known spacing distance. An object may then be placed in the localization field proximate the calibration tool, and the calibration signal may be used to determine the location of the object in the localization field.

As described above, at least some of the plurality of reference points may be adaptively processed with a Kernel function to create a revised three-dimensional coordinate system that reduces, and, after a sufficient number of iterations, diminishes towards zero, the difference between the observed spacing distance and the known spacing distance. An object may be placed within the localization field and its position determined relative to the revised three-dimensional coordinate system.

The catheter catalog may also be used to improve mapping results in the registration of one form of image to another. As discussed in detail in copending U.S. application Ser. No. 11/715,923, incorporated by reference above, it can be desirable to register an the image created in the localization field of the system 8 with an external image, e.g., CT images, magnetic resonance images, ultrasound images, x-ray images, and fluoroscopic images. This image data may be a preacquired image, or it may be acquired real time contemporaneously with the image in the localization field. It is also contemplated that the external image may be an image template rather than an image specific to a particular patient. Further, it is also within the scope of the invention for the external image to be an image generated from position data collected by a localization system. As one of ordinary skill in the art will appreciate, such data is external, as that term is used herein, if it is measured relative to a different origin. Thus, it may come from a different localization system, or from the same localization system relative to a different reference (e.g., localization system data collected during an earlier procedure or measured relative to different electrodes). The external image may be segmented or unsegmented, and may also be derived from another suitable source.

As should be clear from the above discussion, the position information measured by localization system 8 is context-specific to the localization system 8. That is, it describes the position of roving electrodes 17, 52, 54, and 56 relative to the coordinate system of localization system 8. It is often desirable to integrate the position information measured by localization system 8 with an external image such that the position information measured by localization system 8 may be mapped to the external image, which, as described above, utilizes a different coordinate system than localization system 8. This is referred to as "registering" localization system 8 to the external image. Once localization system 8 has been registered to the external image, the position of electrodes 17, 52, 54, and 56, as measured by localization system 8 relative to the coordinate system of localization system 8, can be accurately and precisely illustrated on the external image relative to the coordinate system of the external image.

A method of registering a catheter navigation system (e.g., localization system 8) to a three-dimensional image will be described with reference to FIG. 11, which schematically depicts a system 200 for registering a catheter navigation system to a three-dimensional image. A three-dimensional external image of the heart chamber is obtained, for example by retrieving the external image from a storage medium such as a hard disk, optical disk, or memory that may be part of computer system 220. As described above, the external image may be generated using CT, magnetic resonance, ultrasound, x-ray, fluoroscopy, or another suitable imaging or modeling technique, or may be an image template rather than an image specific to a particular patient. Preferably, the external image includes position information for a plurality of location points on the surface of the heart chamber. Once the external image is obtained, a representation 202 thereof may be displayed on display 223.

A tool (e.g., catheter 13) may then be placed on a first surface location $X_1$ of the heart chamber, for example by robotically navigating catheter 13 into contact with the surface of the heart chamber using a magnetic navigation system, a contact-sensing robotic surgical system or by manually bringing catheter 13 into contact with the surface of the heart chamber. Position information for the first surface location $X_1$ may be measured using localization system 8 as described above (e.g., by measuring at least one characteristic of an electric field or magnetic field at the first surface location $X_1$). This position information is preferably expressed as an (x,y,z) coordinate measured relative to the origin of localization system 8 (e.g., reference electrode 31).

The user then identifies a point $Y_1$ on the three-dimensional external image that corresponds to the first surface location $X_1$ on the surface of the heart chamber. Various imaging techniques, such as fluoroscopy and intracardiac echo (ICE), may be used to aid the user in visualizing the location of catheter 13 on the surface of the heart chamber, thereby simplifying the task of identifying $Y_1$ on the external image. A readily-identifiable anatomical feature and/or the physician's experience and expertise may also be used to verify correspondence between $X_1$ and $Y_1$. For example, if the physician's experience indicates that the first surface location $X_1$ on the surface of the heart chamber is adjacent to the mitral valve, the physician will then identify a point $Y_1$ on the three-dimensional external image that is adjacent to the mitral valve.

In some embodiments of the invention, the first location $Y_1$ is identified by using an input device to identify, or "pick," the first location $Y_1$ on representation 202 of the three-dimensional external image as displayed on display 223. Suitable input devices include, without limitation, keyboards, keypads, pointing devices (e.g., mice, trackballs, and trackpads), two- and three-dimensional joysticks, and active and passive touch-sensitive displays. Preferably, the first location $Y_1$ will have position information expressed as an (x,y,z) coordinate measured relative to the three-dimensional external image.

A fiducial pair $(X_1, Y_1)$ is then created by associating the position information for the first surface location $X_1$, as measured by localization system 8, with the position information for the corresponding first location $Y_1$ on the three-dimensional external image. In some embodiments of the invention, a pairing processor, which may be incorporated into computer system 220, automatically associates the measured position information for first surface location $X_1$ with the position information for the picked point $Y_1$. Thus, the fiducial pair $(X_1, Y_1)$ is a pair of (x,y,z) coordinates, one measured relative to the origin of localization system 8 and one measured relative to the origin of the three-dimensional external image. Multiple fiducial pairs $(X_i, Y_i)$ may be associated using a similar place-and-pick process.

The methodology described above can be referred to generally as a "single pick" implementation, in that the user of system 200 is required only to pick the point $Y_i$ on the external image (e.g., representation 202). Position information for the other element of the fiducial pair, the surface location $X_i$, is determined by measuring the position of catheter 13 relative to localization system 8, and may be automatically associated with the position information for the corresponding point $Y_i$ picked by the user. It is also contemplated, however, to utilize a "dual pick" implementation.

As one of ordinary skill in the art should appreciate, the fiducial pairs may be used to generate a mapping function $f$ that registers localization system 8 to the three-dimensional image. That is, the mapping function $f$ can be used to transform position information expressed according the coordinate system of localization system 8 to position information expressed according to the coordinate system of the three-dimensional image.

For a linear and homogeneous localization system 8, an affine transformation (e.g., translation, rotation, and scaling), such as would result from application of a least mean square error fit, would be suitable. Many localization systems, however, are non-linear and homogeneous, such that an affine transformation may not precisely align the coordinate system of localization system 8 with the coordinate system of the external image. Preferably, therefore, a mapping function is used that locally warps the coordinate system of localization system 8 to force an exact match to the coordinate system of the three-dimensional external image at each fiducial pair, thereby compensating for non-linearities and inhomogeneities in localization system 8. That is, for each fiducial pair $(X_i, Y_i)$, an error function e preferably measures a mapping error (e.g., a divergence between $f(X_i)$ and $Y_i$) of about zero. This can be expressed as $e \equiv |f(X_i)-Y_i| \approx 0$. In some embodiments of the invention, a suitably programmed transform processor incorporated into computer system 20 generates the mapping function $f$.

In one embodiment, the non-linear and non homogeneous localization system's image is corrected using data from the catheter catalog and the three-dimensional lookup table to provide a more homogeneous image. When this image is registered to the external image it will not require as much, if any, local warping of the image to force matches with the external image. This advantageously increases the effectiveness and accuracy of the registration, as well as reduce the number of fiducial pairs required for accurate registration.

The use of the catheter catalog is also effective in registering external real time image data generated contemporaneously with the internal image data. Catheter 13 includes electrode 17 and may also include an ultrasound array (not shown). Catheter 13 and electrode 17 are included in the image data generated by system 8. However, the ultrasound array may not be, in itself, detectable by the localization system 8. Nonetheless, if the catheter 13 has been properly entered into and chosen from the catheter catalog 100, the system 8 may provide an representation of the location of the ultrasound array in the anatomical model.

Moreover, because the information from the catheter catalog, including the orientation of the array relative to the electrode 17, and the distance of the array from electrode 17, allows the localization system 8 to know where the ultrasound array is visualizing, the image data from the ultrasound array is readily registered to the image data from the ultrasound array. In a preferred embodiment multiple electrodes are used to determine the orientation of the catheter and the ultrasound array, e.g., multiple point electrodes arranged in orthogonal pairs.

Although several embodiments of this invention have been described above with a certain degree of particularity, those skilled in the art could make numerous alterations to the disclosed embodiments without departing from the spirit or scope of this invention. For example, the functions of the various processors described herein (e.g., the modeling processor, the error processor, and the correction processor) may be incorporated into one or more processors within one or more computer systems without departing from the spirit and scope of the present invention.

In addition, though the invention has been described in connection with electric or magnetic localization fields, it is contemplated that the invention could also be practiced in connection with an imaging system, such as fluoroscopic imaging, intercardiac echo, magnetic resonance, or the like used for catheter navigation. These imaging systems are regarded as within the meaning of the term "localization field" as used herein.

Further, though this aspect of the invention has been described as utilizing an iteratively-updated lookup table that relates measurements made by the localization system with locations of an object within the localization field, other methodologies are within the spirit and scope of the present invention. For example, algebraic methods, including the use of weighted functions, may be used in place of the lookup table; inhomogeneities in the localization field may be compensated for by adjusting the relative weights of the functions. Similarly, neural network or other machine learning techniques may be utilized.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method for locating features of a catheter for use in a localization system, comprising:
   providing a catheter catalog for use by the localization system, wherein the catheter catalog comprises reference data relating to features of a plurality of catheters, and wherein the reference data comprises electrical characteristics of one or more electrodes on a plurality of catheters;
   providing a catheter having at least one feature, reference data for the provided catheter being within the catheter catalog;
   placing the catheter into a localization field;
   creating a map with the localization field;
   locating the catheter on the map;
   correlating features of the catheter within the localization field with measurements made by the localization system when the features are at various locations.

2. The method according to claim 1, wherein the reference data comprises dimensional data of a plurality of catheters.

3. The method according to claim 2, wherein the dimensional data comprises catheter diameter data of a plurality of catheters.

4. The method according to claim 2, wherein the dimensional data comprises dimensional data pertaining to one or more electrodes on a plurality of catheters.

5. The method according to claim 4, wherein the dimensional data comprises interelectrode spacing data of a plurality of catheters.

6. The method according to claim 2, wherein the dimensional data comprises distal end length data of a plurality of catheters.

7. The method according to claim 2, wherein the dimensional data comprises orientation data.

8. A method for locating features of a catheter for use in a localization system, comprising:
providing a catheter catalog for use by the localization system, wherein the catheter catalog comprises reference data relating to a plurality of features of a plurality of catheters, and wherein the reference data comprises electrical characteristics of one or more electrodes on a plurality of catheters;
providing a catheter having at least a first feature and a second feature, reference data for the provided catheter being within the catheter catalog;
placing the catheter into a localization field generated by the localization system;
locating the first feature of the catheter using the localization system; and
locating the second feature of the catheter using the reference data for the provided catheter from the catheter catalog and the location of the first feature of the catheter according to the localization system.

9. The method according to claim 8, wherein the second feature of the catheter is incapable of being located using the localization system.

10. A method for locating features of a catheter for use in a localization system, comprising:
providing a catheter catalog for use by the localization system, wherein the catheter catalog comprises reference data relating to features of a plurality of catheters;
providing a catheter having a plurality of features, reference data for the provided catheter being within the catheter catalog;
providing a lookup table for use by the localization system, wherein the lookup table comprises data correlating coordinates of an object within a localization field with measurements of a characteristic of the localization field made by the localization system when the object is at various locations;
placing the catheter into the localization field;
using the localization system to measure locations of at least some of the plurality of features of the catheter; and
adjusting the data in the lookup table to reduce a difference between distances between catheter features as measured by the localization system and distances between identical catheter features as provided within the catheter catalog.

11. The method according to claim 10, wherein the step of providing a lookup table for use by the localization system comprises generating a lookup table by predicting reference data for a completely homogeneous localization field.

12. The method according to claim 10, wherein the step of adjusting the data in the lookup table comprises using a Kernel function to update the data in the lookup table.

13. The method according to claim 12, wherein the Kernel function is a decay function, in that adjustments to the data in the lookup table diminish in magnitude as the adjustment point increases in distance from the locations of the catheter features measured by the localization system.

14. The method according to claim 13, wherein the Kernel function is a derivative of a Gaussian curve.

* * * * *